United States Patent
Kiel et al.

(10) Patent No.: US 6,350,724 B1
(45) Date of Patent: Feb. 26, 2002

(54) LICE REMOVING COMPOSITION

(75) Inventors: Jeffrey S. Kiel; Jeffrey H. Ping, both of Gainesville, GA (US)

(73) Assignee: Effcon Laboratories, Inc., Marietta, GA (US)

( * ) Notice: Subject to any disclaimer, the term of this patent is extended or adjusted under 35 U.S.C. 154(b) by 0 days.

(21) Appl. No.: 09/373,951

(22) Filed: Aug. 13, 1999

Related U.S. Application Data

(60) Provisional application No. 60/130,227, filed on Apr. 20, 1999.

(51) Int. Cl.⁷ .............................................. A61K 7/50
(52) U.S. Cl. ................. 510/119; 510/420; 424/405; 424/406; 424/70.1; 514/512; 514/703; 514/739
(58) Field of Search .................. 510/119, 120; 424/405, 406, 70.1; 514/512, 703, 739

(56) References Cited

U.S. PATENT DOCUMENTS

| | | | |
|---|---|---|---|
| 4,193,986 A | 3/1980 | Cox ............................ 424/28 |
| 4,256,600 A | 3/1981 | Lewis et al. ................. 252/132 |
| 4,518,593 A | 5/1985 | Juvin et al. .................. 424/195 |
| 4,774,081 A | 9/1988 | Flashinski et al. ............ 424/78 |
| 4,774,082 A | 9/1988 | Flashinski et al. ............ 424/78 |
| 4,906,488 A | 3/1990 | Pera ........................... 426/573 |
| 4,927,813 A | 5/1990 | Bernstein ..................... 514/65 |
| 4,999,187 A | 3/1991 | Vernon ........................ 424/70 |
| 5,064,859 A | * 11/1991 | Crammer et al. ............ 514/560 |
| 5,079,000 A | 1/1992 | Takahashi et al. ........... 424/195 |
| 5,106,622 A | 4/1992 | Sherwood et al. .......... 424/195 |
| 5,227,163 A | 7/1993 | Eini et al. .................... 424/195 |
| 5,227,406 A | 7/1993 | Beldock et al. ............. 514/703 |
| 5,298,250 A | 3/1994 | Lett et al. .................... 424/405 |
| 5,346,922 A | 9/1994 | Beldock et al. ............. 514/703 |
| 5,411,992 A | 5/1995 | Eini et al. .................... 514/731 |
| 5,518,736 A | 5/1996 | Magdassi et al. ........... 424/451 |
| 5,565,208 A | 10/1996 | Vlasblom .................... 424/405 |
| 5,621,013 A | 4/1997 | Beldock et al. ............. 514/703 |
| 5,648,398 A | 7/1997 | Beldock et al. ............. 514/703 |
| 5,658,584 A | 8/1997 | Yamaguchi ................. 424/405 |
| 5,776,477 A | 7/1998 | Ryder ......................... 424/405 |
| 5,792,465 A | 8/1998 | Hagarty ...................... 424/405 |
| 5,902,595 A | 5/1999 | Burklow et al. ............ 424/405 |
| 5,977,186 A | 11/1999 | Franklin ..................... 514/690 |
| 6,103,248 A | 8/2000 | Burkhart et al. ............ 424/401 |

FOREIGN PATENT DOCUMENTS

| | | |
|---|---|---|
| AU | 7137063 | 12/1971 |
| DE | 3901341 | 7/1990 |
| EP | 0 736 251 A1 | 10/1996 |
| FR | 2 759 546 A | 8/1998 |
| JP | 02 142703 A | 5/1990 |
| JP | 05 039203 A | 2/1993 |
| JP | 2000128720 | 10/1998 |
| WO | WO 98/04128 | 2/1998 |
| WO | WO 99/18800 | 4/1999 |
| WO | WO 200005964 | 7/1999 |
| WO | WO 00/00213 | 1/2000 |

OTHER PUBLICATIONS

Carson et al., American Journal of Diseases of Children, 1988 (vol. 142) pp. 768–769 "Pyrethrins Combined With Piperonyl Butoxide Rid vs 1 Percent Permethrin Nix in the Treatment of Head Lice" (abstract only).

Mumcuoglu, American Entomologist, 1966 (vol. 42) pp. 175–178 "Control of Human Lice (Anoplura: Pediculidae) Infestations: Past and Present" (abstract only).

E. Haubruge et al, Meded. Fac. Landbouwwet, Rijksuniv Gent (vol. 54 No. 3b) (1989) pp. 1083–1093 "The Toxicity of Five Essential Oils Extracted From Citrus Species with Regard to Sitophilus Zeamais Motsch (Col., Curculionidae), Prostephanus Truncatus (Horn)(Col., Bostrychidae) and Tribolium Castaneum Herbst (Col., Tenebrionidae)" (abstract only).

* cited by examiner

*Primary Examiner*—Necholus Ogden
(74) *Attorney, Agent, or Firm*—Sutherland Asbill & Brennan LLP

(57) ABSTRACT

The present invention provides a composition, and a method of use thereof, that is pesticide-free and yet is capable of cleansing an individual of a pest infestation. The composition of the present invention consists essentially of an acid, an alcohol, an aqueous detergent and water. The composition is used in the removal of pests and their ova from infested individuals. Preferably, the composition of the present invention takes the form of a shampoo and is used to cleanse individuals of lice infestations. In use, the composition is applied to hair and allowed to remain in contact with the hair and scalp for a period of time, called the residence time. After the residence time, the composition is rinsed from the hair. Then, the hair is combed with a suitable nit comb. These treatment steps may be repeated as necessary and appropriate to effectuate the removal of the pest infestation.

2 Claims, No Drawings

LICE REMOVING COMPOSITION

RELATED APPLICATIONS

This application claims priority to U.S. Provisional Patent Application, Serial No. 60/130,227, filed on Apr. 20, 1999.

TECHNICAL FIELD

The present invention relates to the removal of pests and their ova. Specifically, the present invention relates to the cleansing of an individual of pests and their ova.

BACKGROUND OF THE INVENTION

Pests present a persistent problem to humans and animals alike. A multitude of products and strategies have been developed to attempt to deal with the problems presented by pests. Unfortunately, most of these products have undesirable side effects. Many of the products make use of pesticides which are often toxic to some extent to humans and animals, those the products are designed to protect. Toxicity problems presented by products containing pesticides can pose risks to those using the products and prevent use by some who are especially sensitive to pesticides. These problems can limit the frequency with which the product can be used and thereby limit the effectiveness of the products in cleansing an individual of a pest infestation. These problems can frequently be exacerbated in children who comprise a significant portion of the population afflicted with pest infestations. Other products designed to repel pests often have unpleasant odors making them undesirable options for dealing with pest problems.

One example of the persistent problems caused by pests is the problem caused by the louse. Lice infestations are a persistent problem worldwide. For example, the annual incidents of lice infestations is estimated to be 10 million cases. Furthermore, many of those infected are school age children. Epidemics can occur in school age children, frequently when schools open in the fall. Because a large number of children are brought together in close proximity for prolonged periods, the chances that lice infestations can spread from child to child greatly increase.

Head lice feed on the blood of their hosts by attaching to the scalp and introducing an anticoagulant under the skin during feeding. This feeding frequently induces erythema and pruritus. The resulting scratching by the host may lead to secondary bacterial infections in addition to causing great discomfort.

Because of the wide spread nature of and the problems caused by lice infestations, many products have been developed to try and treat lice infestations. Most of these products are designed to kill and/or repel the lice. Many of these products contained pesticides which are by their nature toxic to some degree. For example, one common active ingredient in prior commercial products is N,N-diethyl-M-toluamide (DEET). However, DEET has recently been associated with causing various undesirable side effects, such as stinging, damage to mucous membranes, and possibly seizures. In 1989, the Centers for Disease Control issued a cautionary statement regarding the use of DEET. Many other prior art compounds proposed for use as lice treatments have also proven unsuitable for topical application to humans or other animals due to their toxic or noxious effect on the infested individual.

Many of the prior products designed to repel lice have had the disadvantage of having an unpleasant smell. Aside from the discomfort associated with the unpleasant smell, this disadvantage also decreases the likelihood that the treatment product will be used with the recommended frequency. Thus, the efficacy of such products is decreased.

Furthermore, many of the prior art products kill or repel only the pests and not their ova. If a treatment does not rid the individual of the pests' ova, the individual is then faced with re-infestation when the ova hatch.

What is needed in the art is a product that is free of pesticides, but which is still capable of cleansing an individual of a lice infestation. What is needed is a pesticide-free composition and a method of use for that composition that cleanses an individual of pests and their ova. The present invention answers this need by providing a product and a method of use for cleansing an individual of a lice infestation while being substantially free from the disadvantages of the prior commercial products.

SUMMARY OF THE INVENTION

The present invention provides a composition, and a method of use thereof, for cleansing an individual of pests and their ova. By substantially aiding in the removal of undesired pests and their ova, such as lice and their nits, the composition of the present invention acts to cleanse an individual of a pest infestation. The composition of the present invention contains an acid, an alcohol, an aqueous detergent and water. In use, the pest-removing composition can be administered topically to humans, animals or any infested areas.

It is object of the present invention to provide a pesticide-free composition efficacious at removing pests and their ova from infested individuals.

Another object of the present invention is to provide a pest removing composition consisting essentially of an acid, an alcohol, an aqueous detergent and water.

A further object of the present invention is to provide a method of removing pests and their ova from infested individuals using a pesticide-free composition.

Still another object of the present invention is to provide a method of using a pest removing composition consisting essentially of an acid, an alcohol, an aqueous detergent and water to cleanse individuals of pest infestations.

DETAILED DESCRIPTION OF THE PREFERRED EMBODIMENTS

A "pest," as used herein, is meant to include all parasites, such as arthropods, arachnids, triatomes, insects, bugs, flies, lice, fleas, mites, gnats, knits, chiggers, mosquitoes, and ticks, for example. The composition of the present invention is, therefore, intended to be used against all such pests which can be removed by the use of the present invention.

The present invention provides a pest removing composition consisting essentially of an acid, alcohol, an aqueous detergent and water. It should be understood that the composition of the present invention can include other ingredients so long as those ingredients do not interfere with the pest removing ability of the composition.

The invention contains an acid in a concentration of between about 0.01 and 10% w/w. More preferably, the invention contains between about 1 and 8% w/w, and most preferably contains about 5 to 6% w/w. The acid is an ionic or organic acid. Preferably, the acid is hydrochloric acid or acetic acid. More preferably, the acid is glacial acetic acid.

The composition of the present invention also includes an alcohol. Preferably, the alcohol is a short chain alcohol, such as ethanol, propanol or isopropanol. The amount of alcohol in the present invention can range from 1 to 40% w/w. Preferably, the concentration is between about 10 and 30% w/w, and more preferably between about 15 and 25% w/w. Most preferably, the concentration of the alcohol is about 20%. The alcohol is preferably isopropanol.

The composition of the present invention also includes an aqueous detergent. The concentration of the aqueous detergent within the present invention is preferably between about 7 and 21% w/w and more preferably between about 14 and 18% w/w. Preferably, the aqueous detergent is a surfactant, such as sodium laureth sulfate. Sodium laureth sulfate is available in commercial preparations such as Steol® CS-230, which is available from Stepan (North Field, Ill.). Steol® CS-230 is an aqueous preparation of sodium lauryl ether sulfate derived from fatty alcohols, ethoxylated to an average of two moles, and sulfated via a continuous SO3 process. Steol® CS-230 is about 25.5% sodium laureth sulfate. The concentration of Steol® CS-230 within the present invention is preferably between about 30 and 80% w/w and more preferably between about 55 and 70% w/w.

The composition of the present invention may be suitably preserved. Any suitable preservative may be used so long as it does not interfere with the pest removing ability of the composition. For example, in one embodiment of the present invention, methylparaben and propylparaben are included in the composition as preservatives.

The composition of the present invention can contain other ingredients so long as the beneficial, pest-removing nature of the invention is not adversely affected and so long as the pesticide-free nature of the invention is not altered. For example, embodiments of the present invention can contain methylparaben and propylparaben which are antimicrobial agents. Additionally, embodiments of the present invention can contain viscosity modifiers such as sodium chloride or antipruritic agents such as camphor.

The composition of the present invention can be used in different forms, such as a liquid body soap or a shampoo. In other embodiments, the present invention takes the form of a gel, an emulsion, a lotion, an aerosol spray, a mousse, or a cream. Preferably, the composition of the present invention is in the form of a shampoo.

The present invention also includes a method of using the pest removing composition. This method includes applying the composition to the infested area, such as the hair of an individual with a lice infestation. In the case of hair, the composition is applied to the hair. The composition is left on the hair for a period of time referred to as the residence time. The residence time can vary as needed to produce effective results. The residence time can be increased in order to increase the pest removing effectiveness. Alternatively, the residence time can be lowered, for example, in order to decrease any observed irritation to the patient. Preferably, the residence time is between about 1 and 30 minutes. More preferably, the residence time is between about 5 and 20 minutes, and most preferably, the residence time is approximately 10 minutes. At the end of the residence time, the composition is then rinsed from the area of infestation. The hair is then combed with a suitable nit comb. These treatment steps of applying, rinsing and combing can be repeated one or more times to complete the removal of the pest infestation. The time period between uses of the pest removing composition can vary as needed to remove the pest infestation from the individual. Alternatively, the hair can be combed before the composition is rinsed from the area of infestation. The composition of the present invention is advantageous because it allows for frequent use, whereas the use of pesticide-containing compositions can be limited by their inherent toxicity. This ability to use the composition of the present invention increases its effectiveness in cleansing individuals of pest infestations.

Any suitable nit comb can be used in the described method of use of the composition of the present invention. A suitable nit comb may be made of various materials such as metal and plastic. Metal teeth are sturdier and stiffer than those composed of materials such as plastic. Nit combs with metal teeth therefore often last longer than nit combs without metal teeth. The number of teeth and the diameters of the teeth can also vary. The spacing between teeth can also vary; however, the teeth should be close enough to one another to remove nits. The distance between teeth should be 0.3 mm or less, the generally accepted width of nits attached to human hair. Preferably, a nit comb such as the ALB006 is used, which is available from Albyn Stonehaven Ltd. (Stonehaven, Scotland). This comb has 62 metal pins arranged side by side which act as the teeth of the comb. These pins extend approximately 12.5 mm from a plastic piece which acts as the handle of the nit comb. The pins on either end have a diameter of 0.9 mm and the 60 inner teeth have a diameter of 0.6 mm. The gap between the teeth is 0.3 mm.

Without being limited by these theories, it is believed that the composition of the present invention is surprisingly effective because of the synergistic effects of the composition's ingredients. It is believed that the composition of the present invention affects pests, such as lice, sufficiently such that they may be washed and removed from the infested region. Furthermore, in the cases of some pests, such as lice, it is believed that the composition of the present invention aids in the removal of the pests' ova by "loosening" or "breaking down" the substances some pests use to attach their ova to their hosts.

The effectiveness of the present invention at cleansing an individual of a pest infestation is further surprising because the composition of the present invention is neither pediculicidal nor ovicidal in standard in vitro tests used by those skilled in the art to test pest treatments.

EXAMPLES

The following specific examples will illustrate several embodiments of the present invention. It will be appreciated that other examples will be apparent to those of ordinary skill in the art and that the invention is not limited to these specific illustrative examples.

Example I

Production of a Pest Removing Composition

The following components were combined in approximate relative amounts to produce a pest removing composition.

| | |
|---|---|
| Synthetic Camphor | 0.75% w/w |
| Acetic Acid | 6.0% w/w |
| Isopropanol | 20.0% w/w |
| Steol ® CS-230 | 46.0% w/w |
| Methylparaben | 0.2% w/w |
| Propylparaben | 0.1% w/w |
| Purified Water | q.s. |

The alcohol was transferred into a mixing vessel. The camphor was added to this vessel and mixed until completely dissolved. The methylparaben and propylparaben were added next and mixed until fully dissolved. The acetic acid was then added and mixed until completely uniform. Next, the Steol® CS-230 was added and mixed until uniform. Finally, purified water was added to bring the composition up to its target weight.

Example II

Production of a Two Component Pest Removing Composition

Each component of the composition was produced and stored separately. The two components were mixed just prior to use. The first component was an "Alcohol/Detergent Component" and the second component was an "Acetic Acid Component." The two component composition was prepared in the following manner.

The following ingredients were combined in approximate relative amounts to make the "Alcohol/Detergent Component."

| Isopropanol | 22.64% w/w |
| Methylparaben | 0.2% w/w |
| Propylparaben | 0.1% w/w |
| Steol ® CS-230 | 62.83% w/w |
| Purified Water | 14.23% w/w |

The isopropanol and the methylparaben and propylparaben were mixed in a vessel until the parabens were completely dissolved. A portion of the Steol® CS-230 was then added and mixed until completely uniform. The purified water was then added and mixed until uniform. Steol® CS-230 was then used to dilute the mixture to its final weight and mixed until completely uniform.

The following ingredients were combined in approximate relative amounts to produce the "Acetic Acid Component."

| Acetic Acid | 42.86% w/w |
| Methylparaben | 0.2% w/w |
| Propylparaben | 0.1% w/w |
| Purified Water | q.s. |

Purified water was added to a mixing vessel. Glacial acetic acid was added to the vessel and mixed until completely uniform. The methylparaben and propylparaben were then added to the mixing vessel and mixed until completely dissolved. The resulting solution was then diluted to the final target weight with purified water.

The two components were mixed together at the point of use in relative amounts such that the "Acetic Acid Component" comprised approximately 11⅔% of the final combined product. The final product contained the following ingredients in the approximate relative amounts listed below.

| Isopropanol | 20.0% w/w |
| Methylparaben | 0.2% w/w |
| Propylparaben | 0.1% w/w |
| Steol ® CS-230 | 55.5% w/w |
| Acetic Acid | 5.0% w/w |
| Purified Water | 19.2% w/w. |

Example III

Production of a Pest Removing Composition

The following components were combined in approximate relative amounts to produce a pest removing composition.

| Isopropanol | 20.0% w/w |
| Methylparaben | 0.2% w/w |
| Propylparaben | 0.1% w/w |
| Glacial Acetic Acid | 5.0% w/w |
| Purified Water | 19.2% w/w |
| Steol ® CS-230 | 55.5% w/w |

The isopropanol and the methylparaben and propylparaben were mixed in a vessel until the parabens were completely dissolved. Glacial acetic acid was added to the vessel and mixed until completely uniform. A portion of the Steol® CS-230 was then added and mixed until completely uniform. The purified water was then added and mixed until uniform. Steol® CS-230 was then used to dilute the mixture to its final weight and mixed until completely uniform.

Example IV

Removal of Lice Using the Pest Removing Composition

The composition described in Example III was used in a double-blind study. Health Care professionals applied the study composition, collected lice and nits for viability assessments, used nit combs to remove nits from the hair after treatment, and performed all assessments of infestation. All qualified patients were treated with the study composition on Day 1 and could be treated on Day 15 of the study, if signs of infestation were present. The study period for an individual patient was up to approximately 29 days.

Patients were eligible to participate in the study if they signed informed consent, were at least 2 years old at screening, and had a head lice infestation confirmed by the presence of at least two live lice and at least 20 apparently viable nits. Patients were excluded from the study if they had been treated for pediculosis within four weeks before the screening evaluation, had an infestation of body or pubic lice, or had concurrent medical conditions that would interfere with efficacy and safety evaluations or put the patient at unacceptable risk. Only one member of a household was allowed to participate, and study personnel explained adjunctive measures to remove lice and nits from the home environment to reduce the possibility of re-infestation.

Ten apparently viable nits were collected before treatment by cutting the hair with nits attached. Each nit was examined under a dissecting microscope, and any nits which did not appear viable were discarded and replaced. Study treatments were applied to dry hair until saturated and then were allowed to remain in contact with the hair and scalp for 10 minutes before being rinsed out. Lice and nits were recovered from the rinse water by straining it through a cloth filter. Ten additional apparently viable nits were collected after treatment but before nit combing began. Subsequently, the nit comb was used for up to 20 minutes to remove any lice or nits remaining in the hair.

The viability of lice collected after treatment was evaluated within 1 hour after collection and after being incubated at $31.7\pm0.50°$ C. ($89°$ F.) and $50\pm10\%$ relative humidity for $24\pm2$ hours. The viability of nits collected before and after treatment was assessed after incubation at $31.7\pm0.5°$ C. ($89°$ F.) and $50\pm10\%$ relative humidity for 14 days.

Patients were examined on Day 15 and could be treated again if signs of infestation were present and all lice collected on Day 1 were dead after incubation for 24 hours. A patient could be discontinued as a treatment failure at Day 15 if signs of infestation were present, and one or more lice collected after treatment were alive after incubation. Clinical outcome was recorded as cured, re-infestation, or treatment failure 14 days after the last application of study treatment.

This study was conducted in two stages. In each stage, 10 patients were treated with the study composition. The 20 patients exposed to the study composition consisted of 15 females and 5 males who ranged in age from 7 to 14 years. At screening, 9 (45%) patients had moderate infestations (11–20 live lice), and 11 (55%) patients had severe infestations (>20 live lice).

Viability assessments are shown in Table 1 for lice recovered and incubated after treatment and for nits collected before and after treatment on Day 1. If a second treatment was applied, lice and nits were not collected. At 1 hour after treatment, the percent of lice still alive was 44.6% in Stage 1 and 34.0% in Stage 2. After incubation, 6/231 (2.6%) lice in Stage 1, and 0/215 (0%) lice in Stage 2 were still alive.

TABLE 1

|  | Stage 1 (N = 10) | Stage 2 (N = 10) |
|---|---|---|
| Number of Lice[1] | | |
| VISIT 1: 1 HOUR AFTER TREATMENT | | |
| Total Number Incubated | 231 (100%) | 215 (100%) |
| Number Live | 103 (44.6%) | 73 (34.0%) |
| Number Dead | 128 (55.4%) | 142 (66.0%) |
| VISIT 1: 24 HOURS AFFER TREATMENT | | |
| Total Number Incubated | 231 (100%) | 215 (100%) |
| Number Live | 6 (2.6%) | 0 (0.0%) |
| Number Dead | 225 (97.4%) | 215 (100%) |
| Number of Nits[2] | | |
| VISIT 1: PRE-TREATMENT (DAY 1) | | |
| Total Number Incubated | 100 (100%) | 100 (100%) |
| Number Hatched | 89 (89%) | 93 (93%) |
| Number Not Hatched | 11 (11%) | 7 (7%) |
| VISIT 1: POST-TREATMENT (DAY 1) | | |
| Total Number Incubated | 100 (100%) | 100 (100%) |
| Number Hatched | 77 (77%) | 90 (90%) |
| Number Not Hatched | 23 (23%) | 10 (10%) |

[1]Lice were collected from the hair and scalp, rinse water, or towel used to dry the hair after treatment. Viability was assessed 1 hour after treatment and after 24 hours of incubation.
[2]For each patient, 10 viable nits were collected before application of the study composition, and 10 viable nits were collected after treatment with the study composition prior to nit combing. Viability assessments were completed following incubation for 14 days.

The severity of infestation based on the number of lice or nits on the hair is summarized in Tables 2 and 3. The severity of infestation decreased at each evaluation after treatment on Day 1.

TABLE 2

| Severity of Infestation | Stage 1 (N = 10) | Stage 2 (N = 10) |
|---|---|---|
| VISIT 1: DAY 1 | | |
| None (0 live lice) | 0 (0%) | 0 (0%) |
| Mild (1–10 live lice) | 0 (0%) | 0 (0%) |
| Moderate (11–20 live lice) | 4 (40%) | 5 (50%) |
| Severe (>20 live lice) | 6 (60%) | 5 (50%) |

TABLE 2-continued

| Severity of Infestation | Stage 1 (N = 10) | Stage 2 (N = 10) |
|---|---|---|
| VISIT 2: DAY 15 | | |
| None (0 live lice) | 2 (20%) | 1 (10%) |
| Mild (1–10 live lice) | 4 (40%) | 7 (70%) |
| Moderate (11–20 live lice) | 4 (40%) | 2 (20%) |
| Severe (>20 live lice) | 0 (0%) | 0 (0%) |
| VISIT 3: DAY 29 | | |
| Number Evaluated | 3[1] | 9[2] |
| None (0 live lice) | 3 (30%) | 8 (80%) |
| Mild (1–10 live lice) | 0 (0%) | 1 (10%) |
| Moderate (11–20 live lice) | 0 (0%) | 0 (0%) |
| Severe (>20 live lice) | 0 (0%) | 0 (0%) |

[1]Five patients were considered treatment failures at Day 15 because one or more lice collected on Day 1 were alive after incubation. These five patients did not receive a second treatment. Two patients were considered to be cured 14 days after the first treatment.
[2]One patient was considered to be cured 14 days after the first treatment.

TABLE 3

| Severity of Infestation | Stage 1 (N = 10) | Stage 2 (N = 10) |
|---|---|---|
| VISIT 1: DAY 1 | | |
| Grade 0 (0 nits) | 0 (0%) | 0 (0%) |
| Grade 1 (1–9 nits) | 0 (0%) | 0 (0%) |
| Grade 2 (10–40 nits) | 3 (30%) | 5 (50%) |
| GRADE 3 (>40 MTS) | 7 (70%) | 5 (50%) |
| VISIT 2: DAY 15 | | |
| Grade 0 (0 nits) | 2 (20%) | 1 (10%) |
| Grade 1 (1–9 nits) | 5 (50%) | 6 (60%) |
| Grade 2 (10–40 nits) | 3 (30%) | 3 (30%) |
| GRADE 3 (>40 MTS) | 0 (0%) | 0 (0%) |
| VISIT 3: DAY 29 | | |
| Number Evaluated | 3[1] | 9[2] |
| Grade 0 (0 nits) | 3 (30%) | 8 (80%) |
| Grade 1 (1–9 nits) | 0 (0%) | 1 (10%) |
| Grade 2 (10–40 nits) | 0 (0%) | 0 (0%) |
| GRADE 3 (>40 MTS) | 0 (0%) | 0 (0%) |

[1]Five patients were considered treatment failures at Day 15 because one or more lice collected on Day 1 were alive after incubation. These five patients did not receive a second treatment. Two patients were considered to be cured 14 days after the first treatment.
[2]One patient was considered to be cured 14 days after the first treatment.

Clinical outcome is summarized in Table 4. Five patients in Stage 1 were considered to be treatment failures at Day 15 because one or more lice collected on Day 1 were alive after being incubated for 24 hours. These five patients did not receive a second treatment. The remaining five patients in Stage 1 and eight patients in Stage 2 were cured of their head lice infestations 14 days after the final application of the study composition. Two patients in Stage 1 and one patient in Stage 2 were cured after a single treatment.

TABLE 4

| Clinical Outcome | Stage 1 (N = 10) | Stage 2 (N = 10) |
|---|---|---|
| Cured | 5 (50%) | 8 (80%) |
| Re-Infestation | 0 (0%) | 0 (0%) |
| Treatment Failure | 5 (50%)[1] | 2 (20%) |

[1]A second treatment was not applied on Day 15 for these five patients.

It should be understood that the foregoing relates to particular embodiments of the present invention, and that numerous changes may be made therein without departing from the scope of the invention.

What is claimed is:

1. A composition for removing a pest and its ova from an individual consisting essentially of an acid selected from the group consisting of an acetic acid or a hydrochloric acid in a concentration of between about 0.01 and 10% w/w; an alcohol selected from the group consisting of isopropanol, propanol and ethanol in a concentration of between about 10 and 30% w/w; an aqueous detergent in a concentration of between about 7 and 21% w/w; and water.

2. A composition for removing a pest and its ova from an individual consisting essentially of an acid selected from the group consisting of an acetic acid or a hydrochloric acid in a concentration of about between about 1 and 8% w/w; an alcohol selected from the group consisting of isopropanol, propanol and ethanol in a concentration of between about 15 and 25%, an aqueous detergent in a concentration of between about 7 and 21% w/w, and water.

* * * * *